United States Patent [19]
Wylie et al.

[11] Patent Number: 5,983,703
[45] Date of Patent: Nov. 16, 1999

[54] ANALYTICAL ENGINE FOR GAS CHROMATOGRAPH

[75] Inventors: David A. Wylie, Unionville; Ori D. Raubvogel; Richard C. Leveson, both of North York, all of Canada

[73] Assignee: Perkin-Elmer (Canada) Ltd., Montreal, Canada

[21] Appl. No.: 08/709,789

[22] Filed: Sep. 9, 1996

[51] Int. Cl.$^6$ .......................... G01N 30/30; G01N 30/02; H05B 1/02

[52] U.S. Cl. .......................... 73/23.42; 73/23.35; 422/89; 422/93

[58] Field of Search ............... 73/23.42, 23.35, 73/23.41; 422/89, 93

[56] References Cited

U.S. PATENT DOCUMENTS

| | | | |
|---|---|---|---|
| 1,694,725 | 12/1928 | Tabb | 219/521 |
| 2,907,861 | 10/1959 | Melton | 219/43 |
| 3,028,473 | 4/1962 | Dyer et al. | 219/20 |
| 3,122,014 | 2/1964 | Dobbins | 73/23 |
| 3,581,573 | 6/1971 | Purcell | 73/422 |
| 3,800,602 | 4/1974 | Jones | 73/23.1 |
| 3,858,435 | 1/1975 | Stevens | 73/23.1 |
| 4,044,593 | 8/1977 | Haruki et al. | 73/23.1 |
| 4,088,458 | 5/1978 | Jourdan | 55/197 |
| 4,173,145 | 11/1979 | Durbin | 73/422 GC |
| 4,351,385 | 9/1982 | Amey | 165/61 |
| 4,353,243 | 10/1982 | Martin | 73/23.1 |
| 4,367,645 | 1/1983 | Froment | 73/23.1 |
| 4,888,295 | 12/1989 | Zaromb et al. | 436/161 |
| 5,005,399 | 4/1991 | Holtzclaw et al. | 73/23.39 |
| 5,034,193 | 7/1991 | Maroulis et al. | 422/89 |
| 5,083,742 | 1/1992 | Wylie et al. | 251/61.1 |
| 5,093,269 | 3/1992 | Leichnitz et al. | 436/178 |
| 5,176,359 | 1/1993 | Leveson et al. | 251/61.1 |
| 5,197,192 | 3/1993 | Wylie et al. | 29/890.13 |
| 5,205,845 | 4/1993 | Sacks et al. | 55/197 |
| 5,289,715 | 3/1994 | Staples et al. | 73/24.01 |
| 5,298,225 | 3/1994 | Higdon | 422/89 |
| 5,338,514 | 8/1994 | Morabito et al. | 422/89 |
| 5,340,543 | 8/1994 | Annino et al. | 422/89 |
| 5,376,277 | 12/1994 | Cortes et al. | 210/659 |
| 5,392,634 | 2/1995 | Asano et al. | 73/23.42 |
| 5,472,670 | 12/1995 | Harrington et al. | 422/89 |
| 5,544,276 | 8/1996 | Loux et al. | 392/480 |
| 5,591,406 | 1/1997 | Hirai et al. | 422/80 |
| 5,611,846 | 3/1997 | Overton et la. | 96/102 |

FOREIGN PATENT DOCUMENTS

| | | |
|---|---|---|
| 0 723 150 A2 | 7/1996 | European Pat. Off. . |
| 0 499 445 A2 | 8/1992 | Germany . |

OTHER PUBLICATIONS

The Valco Model VIII, *Model VIII Diaphragm Valves, Injection, Switching, and Stream Selection Valves*, pp. 217–219.

*Primary Examiner*—Hezron Williams
*Assistant Examiner*—J. David Wiggins
*Attorney, Agent, or Firm*—Skjerven, Morrill, MacPherson, Franklin & Friel, LLP; J. Krause-Polstorff; David M. Sigmond

[57] ABSTRACT

An assembly of chromatograph components which operate at a uniform elevated or reduced temperature and perform the functions of sample injection, precolumn backflush, analytical column selection, detection in a reduced mass and volume, and with a reduced surface area for reduced power consumption in accordance with use in a portable gas chromatograph is disclosed. Parts of the assembly including a switching valve assembly, a column plate, a thermal cover and a detector block are thermally-linked and those parts of the assembly which contact the sample including the gas chromatograph columns are maintained at a controlled temperature using, for example, an efficient axial heater, a Peltier cooler or a heat pipe and temperature sensors, thereby increasing analytical confidence.

70 Claims, 5 Drawing Sheets

ANALYTICAL ENGINE FOR GAS CHROMATOGRAPH

CROSS-REFERENCE TO RELATED APPLICATIONS

This application relates to the co-pending application Ser. No. 08/709,855, filed on the same day, entitled "IMPROVED FLUID CONTROL VALVE ARRANGEMENT", by Wylie and Raubvogel, owned by the assignee of this application and incorporated herein by reference.

BACKGROUND OF THE INVENTION

In a gas chromatograph, a sample is introduced onto the head of a gas chromatograph column and is carried towards the detector by a carrier gas. The sample components become separated from one another as they travel the length of the column by virtue of differences in their rates of interaction with the sorptive material coating the inside walls of the column or coated onto a substantially inert support material packed into the column. The different sample components are therefore retained for different lengths of time within the column, and arrive at the detector at characteristic times. These "retention times" are used to identify the particular sample components, and are a function of the type and amount of sorptive material in the column, the column length and diameter, the carrier gas type and flowrate, and of the column temperature. In order to have repeatable retention times, the column temperature must also be repeatable. Because a gas chromatograph must operate in a range of ambient temperatures, the gas chromatograph must be controllably heated to a temperature greater than the highest expected ambient temperature in order to achieve repeatable retention times.

The gas chromatograph analysis is complete once all the sample components have traversed the column length and have flowed through the detector. The analysis time is therefore determined by the retention time of the most-retained sample component.

If a second sample is introduced onto a gas chromatograph column before the first analysis is completed, the potential exists for little-retained components from the second sample to flow through the detector concurrently with more-retained components from the first sample. This situation leads to difficulty in interpreting the detector output signal. To avoid this situation a technique known as "precolumn backflushing" is used. Two gas chromatograph columns, typically a shorter precolumn and a longer analytical column, are joined in series with a tee between the columns. Initially, the branch of the tee is closed to flow and carrier gas is directed along the precolumn and analytical column in series. A sample is introduced onto the head of the precolumn and carried along the precolumn towards the analytical column. After an interval, and using suitable carrier gas switching valves, vents and control timing, the carrier gas is introduced at the branch of the tee between the two columns. Sample components which have already passed the tee continue to be carried towards the detector along the analytical column. Those which are still in the precolumn are flushed backwards along the precolumn and vented from the head of the precolumn. Backflushing of the precolumn to clean it for the next sample occurs concurrently with analysis on the analytical column. Once all components have eluted from both columns, the carrier gas is switched to flow through both columns in series and the system is ready to accept the next sample.

Precolumn backflushing beneficially reduces total analysis time because it is not necessary to wait for the more retained components which are not required to be analyzed to traverse the analytical column. Hence, the analytical confidence is increased by reducing the possibility of coelution.

In a gas chromatograph, the types of sample components which can be separated from one another prior to detection are determined by the type of gas chromatograph column used. Some column types are suited to light gases, others to heavier vapors, and yet others to polar vapors. For flexibility in types of chemical components which can be analyzed in a gas chromatograph, it is beneficial to have several different types of columns available for installation so that the optimum column can be selected for the particular analysis desired.

When a large volume of a sample exists, as in ambient air sampling, a sample can be introduced automatically into a gas chromatograph by means of a gas sampling loop. A suction pump draws the sample through a defined volume. With appropriate valving and controls, the carrier gas is momentarily diverted through this volume to deliver the entire sample, or a defined aliquot of it, onto the head of the column for analysis. Where only a small volume of sample exists, as in a vessel of a sample collected from a process or from a remote location, an aliquot of the sample can be introduced manually onto the head of the gas chromatograph column using a hypodermic type syringe. An appropriate syringe injection port with resealable septum is fitted at the column head. For flexibility in analyzing samples from both types of sources, it is beneficial for a gas chromatograph to provide for both types of sample introduction.

In a gas chromatograph it is beneficial for all parts which contact the sample to be chemically-inert, non-sorptive and also to be maintained at an elevated temperature. The quality of the analysis is preserved by reducing sample degradation through chemical reaction of sample components with and adsorption of sample components onto gas chromatograph parts. Minimizing the sample flow path further reduces the possibility of sample degradation by contact.

In a hand-carried, battery-powered portable gas chromatograph it is desirable to have a low mass for ease of portability, and also to have a long operating time so that the user need not carry extra batteries or return frequently to a battery-charging station. Lightweight and low-power electronic components are available for instrumentation amplifiers, displays, indicators, and controls so that most of the power consumed by a gas chromatograph is used in elevating the temperature of the gas chromatograph's parts and in maintaining the parts at elevated temperature.

SUMMARY OF INVENTION

The invention comprises an assembly of chromatograph components, hereinafter referred to as an analytical engine, which operate at an elevated or reduced temperature and perform the functions of sample injection, precolumn backflush, analytical column selection, and detection in a reduced mass and volume and with a reduced surface area for reduced power consumption suitable for use in a portable gas chromatograph. Parts of the assembly comprising a switching valve assembly, a column plate, a thermal cover and a detector block are thermally-linked and those parts of the assembly which contact the sample including the gas chromatograph columns are maintained at a controlled temperature using, for example, an efficient axial heater, a Peltier cooler or a heat pipe and temperature sensors, thereby increasing analytical confidence. In accordance with this invention, the temperature control means need not be mounted axially, for example, a Peltier cooler may be mounted proximate the thermal cover.

The gas chromatograph columns include a precolumn and a plurality of analytical columns. The analytical engine assembly provides for sample loop injection onto a precolumn, syringe injection onto a precolumn and injection of a sample from a precolumn onto one of the analytical columns. The analytical engine can also be configured to accomplish very complex sample manipulation, such as variable precolumn separation timing, sample splitting onto different analytical columns, and multiple detector selection.

The reduced mass, volume, and power consumption of the analyzer are well-suited to any analysis application where space or power or both are constrained or where very rapid thermal cycling is required. Applications include on-line process applications, remote, unattended monitoring applications, bedside use for analyzing exhaled breath of patients, use in airborne, space or undersea operations, and also laboratory use where bench space is limited.

DETAILED DESCRIPTION OF THE INVENTION

Figure 1A:
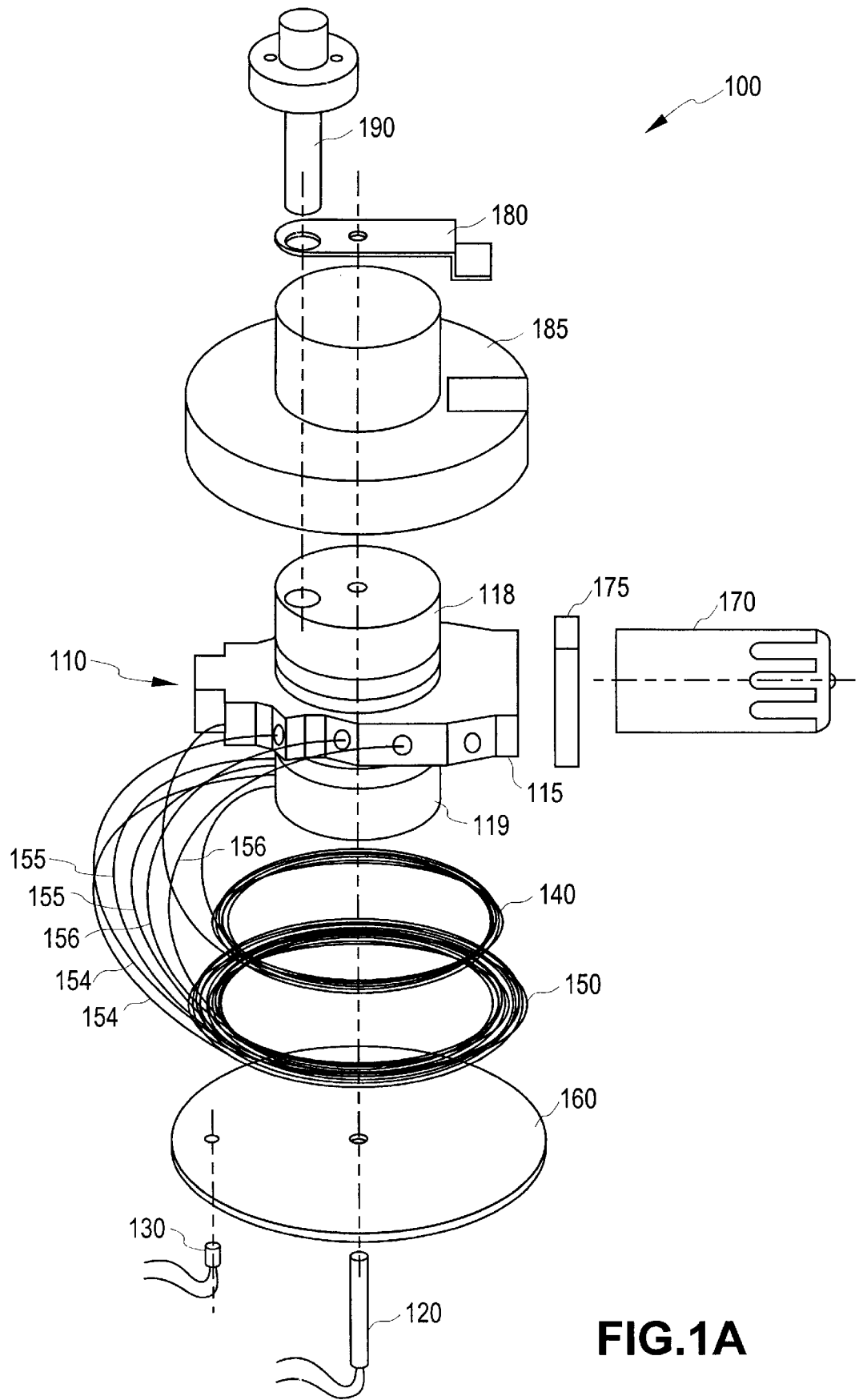
FIG. 1a shows an exploded view of an analytical engine for gas chromatography having an electric heater in accordance with an embodiment of this invention.

FIG. 1a shows an exploded view of an analytical engine for gas chromatography in accordance with one embodiment of this invention. Analytical engine 100 includes switching valve assembly 110 (part of which is valve block 115), heating element 120, temperature sensing element 130, gas chromatograph precolumn 140, three gas chromatograph analytical columns 154, 155, and 156, column plate 160, detector block 175, lamp holder 170, detector thermal link 180, syringe injection port 190, and thermal cover 185.

Switching valve assembly 110 is a fluid control valve arrangement (such as disclosed in above referenced co-pending application Ser. No. 09/709,855) which performs numerous functions. In accordance with this invention, switching valve assembly 110 performs the functions of filling sample loop 210 (see FIG. 2 and FIG. 3), injection of sample loop 210 contents onto precolumn 140, syringe injection onto precolumn 140, and injection of sample from precolumn 140 onto one of three analytical columns 150, which include a low-retention column 154, a medium-retention column 155, or high-retention column 156. Additional functions performed by switching valve assembly 110 are maintenance of flow to vent through two of three analytical columns 150 when not selected, backflushing of retained components from precolumn 140 to precolumn backflush vent 250 (see FIG. 2), injection of the sample from selected one of analytical columns 154, 155, or 156 into detector block 175 and also injection of the sample from sample loop 210 directly into detector block 175 via low retention analytical column 154, bypassing precolumn 140.

Switching valve assembly 110 in one embodiment is a multilayer inert membrane blister valve assembly of 21 interconnected valve elements where in one embodiment analytical valve interconnections are made on layers other than those having the membrane blisters. The multilayer valve assembly comprises a pair of driver plates, a pair of membranes with developed blisters, and a pair of seat plates symmetrically positioned about valve block 115 (see related application Ser. No. 08/709,855 by Wylie and Raubvogel, "IMPROVED FLUID CONTROL VALVE ARRANGEMENT" referenced above). Having interconnections on layers other than those associated with the blisters allows a maximum number of valves to be packaged in a minimum volume with a minimum of external interconnections.

Valve block 115 of switching valve assembly 110 functions as a manifold for the connection of precolumn 140, analytical columns 150 (comprising analytical column 154, analytical column 155, and analytical column 156), and detector block 175 to switching valve assembly 110. Pneumatic support components external to analytical engine 100 also connect to valve block 115. In one embodiment there are a total of 12 compression fittings on valve block 115 for connection of gas chromatograph columns and pneumatic support components. The pneumatic support components include a supply of compressed pressure-regulated carrier gas fed in on carrier gas input 220 (see FIG. 2) for carrying a sample along analytical columns 154, 155, and 156, an attachment at out-to-suction pump 230 (see FIG. 2) of a suction pump for collecting a gas sample or vapor sample for analysis, an inlet filter to remove particulates from a gas or vapor sample, and a gas flow restrictor on precolumn backflush vent 250 (see FIG. 2) to minimize carrier gas consumption. In one embodiment, pneumatic connections to pilot valves for supplying pressurized nitrogen as driver fluid to operate the membrane valves are made through fittings in the lower face of switching valve assembly 110. In one embodiment, the pressure of the driver fluid is maintained at between 15 and 42 psi above the column head pressure. Driver fluid consumption is typically less than 1 mL/minute.

Precolumn 140 is a relatively short and unretentive column which in one embodiment is a 4 m length of 0.53 mm inner-diameter stainless steel tubing coated on the inside with 2.0 $\mu$m of poly(35%-diphenyl-65%-dimethylsiloxane). Three analytical columns 150 are selected from a group of columns of varying retention depending on the specific application. For analysis of a range of airborne volatile organic compounds, low retention column 154 used in one embodiment is an 8 m long deactivated fused silica capillary tube having an inner diameter of 0.25 mm. In one embodiment of this invention, medium retention analytical column 155 that is a 20 m long capillary tube of fused silica having an inner diameter of 0.32 mm and being coated on the inside with a 1.0 $\mu$m thick coating of poly(ethylene glycol) is used. High retention analytical column in one embodiment is a 15 m long fused silica capillary tube having an inner diameter of 0.32 mm with a 12 $\mu$m coating of 100% methyl silicone.

Figure 2:
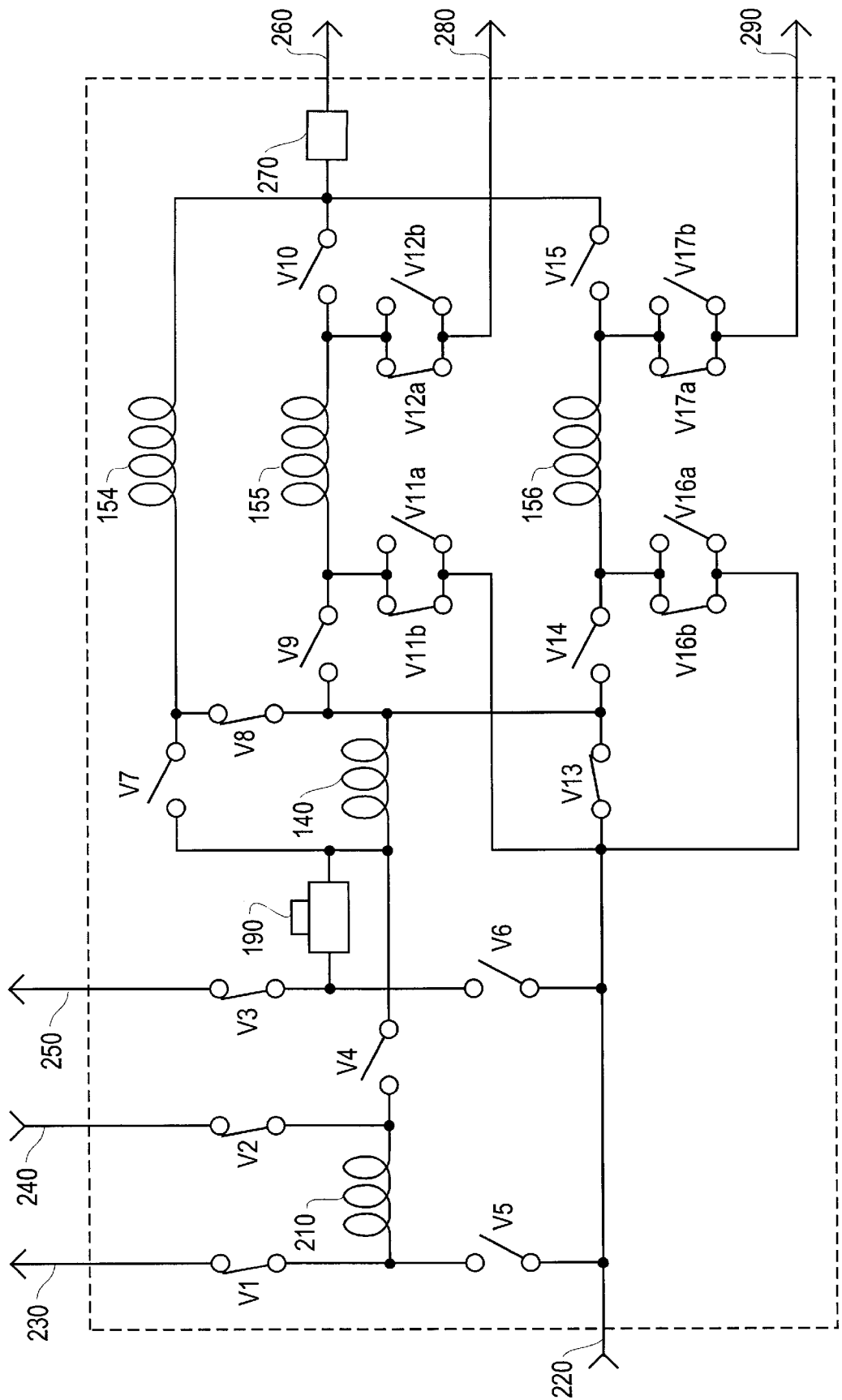
FIG. 2 shows a pneumatic diagram of the analytical engine with switching valves V1–V10, V13–V15, V11A, V11B, V12A, V12B, V16A, V16B, V17A, V17B in accordance with an embodiment of this invention.

FIG. 2 shows a schematic pneumatic diagram of analytical engine 100 with switching valves V1–V10, V13–V15, V11A, V11B, V12A, V12B, V16A, V16B, V17A, V17B.

Table 1 gives a list of functions performed by analytical engine 100, the corresponding position (either permitting or blocking flow) of each of the switching valves shown in FIG. 2, and the remote pilot valves (not shown) which admit a pressurized gas in order to operate the switching valves. In what is to follow, "STATE" refers to the corresponding functions being performed by the arrangement of the switching valves represented in FIG. 2. FIG. 2 shows the switching valves in the positions corresponding to STATE 1 in Table 1. In one embodiment, switching valves V11A and V11B, V12A and V12B, V16A and V16B, and V17A and V17B, respectively, are arranged in parallel. Actuating each one of a pair of parallel switching valves with different pilot valves allows a reduction of the total number of pilot valves needed to perform the required functions. Table 2 shows the correspondence between the switching valves and the pilot valves which actuate them.

TABLE 1

| STATE | Functions | Switching Valves Permitting Flow | Switching Valves Blocking Flow | Pilot Valves Actuated |
|---|---|---|---|---|
| 1 | Sample loop 210 fill; Precolumn 140 Backflush; Analytical Column 154 feeding Detector 270; Analytical Column 155 flushing to Vent 280; Analytical Column 156 flushing to Vent 290 | V1, V2, V3, V8, V11B, V12A, V13, V16B, V17A | V4, V5, V6, V7, V9, V10, V11A, V12B, V14, V15, V16A, V17B | none |
| 2 | Inject Sample Loop 210 onto Precolumn 140; Analytical Column 154 feeding Detector 270; Analytical Column 155 flushing to Vent 280; Analytical Column 156 flushing to Vent 290 | V4, V5, V8, V11B, V12A, V16B, V17A | V1, V2, V3, V6, V7, V9, V10, V11A, V12B, V13, V14, V15, V16A, V17B | 1, 3 |
| 3 | Inject Sample Loop 210 onto Precolumn 140; Precolumn 140 feeding Analytical Column 155; Analytical Column 155 feeding Detector 270; Analytical Column 156 flushing to Vent 290 | V4, V5, V9, V10, V16A, V17B | V1, V2, V3, V6, V7, V8, V11A, V11B, V12A, V12B, V13, V14, V15, V16B, V17A | 1, 3, 5, 6 |
| 4 | Inject Sample Loop 210 onto Precolumn 140; Precolumn 140 feeding Analytical Column 156; Analytical Column 156 feeding Detector 270; Analytical Column 155 flushing to Vent 280 | V4, V5, V11A, V12B, V14, V15 | V1, V2, V3, V6, V7, V8, V9, V10, V11B, V12A, V13, V16A, V16B, V17A, V17B | 1, 3, 5, 7 |
| 5 | Precolumn 140 Backflush; Analytical Column | V1, V2, V3, V9, V10, V13, | V4, V5, V6, V7, V8, V11A, | 5, 6 |

TABLE 1-continued

| STATE | Functions | Switching Valves Permitting Flow | Switching Valves Blocking Flow | Pilot Valves Actuated |
|---|---|---|---|---|
|  | 155 feeding Detector 270; Analytical Column 156 flushing to Vent 290 | V16A, V17B | V11B, V12A, V12B, V14, V15, V16B, V17A |  |
| 6 | Precolumn 140 Backflush; Analytical Column 156 feeding Detector 270; Analytical Column 155 flushing to Vent 280 | V1, V2, V3, V11A, V12B, V13, V14, V15 | V4, V5, V6, V7, V8, V9, V10, V11B, V12A, V16A, V16B, V17A, V17B | 5, 7 |
| 7 | Syringe Injection onto Precolumn 140; Precolumn 140 feeding Analytical Column 154; Analytical Column 154 feeding Detector 270; Analytical Column 155 flushing to Vent 280; Analytical Column 156 flushing to Vent 290 | V6, V8, V11B, V12A, V16B, V17A | V1, V2, V3, V4, V5, V7, V9, V10, V11A, V12B, V13, V14, V15, V16A, V17B | 2, 3 |
| 8 | Inject Sample Loop 210 onto Analytical Column 154; Bypass Precolumn 140; Analytical Column 154 feeding Detector 270 | V4, V5, V7 | V1, V2, V3, V6, V8, V9, V10, V11A, V11B, V12A, V12B, V13, V14, V15, V16A, V16B, V17A, V17B | 1, 3, 4, 5 |

TABLE 2

| Pilot Valve | Switching Valve |
|---|---|
| 1 | V4, V5 |
| 2 | V6 |
| 3 | V1, V2, V3, V13 |
| 4 | V7 |
| 5 | V8, V11A, V12A, V16A, V17A |
| 6 | V9, V10, V16B, V17B |
| 7 | V11B, V12B, V14, V15 |

With reference to FIG. 2 and Table 1, a typical analysis using sample loop injection proceeds as follows below.

Initially, switching valves are in STATE 1 to fill sample loop 210 (see also FIG. 3) on sample input 240 using the external pump (not shown). In particular, with valves V1 and V2 open, the sample is drawn in from input 240 to sample loop 210 by the suction pump (not shown) attached at out-to-suction pump 230. Carrier gas enters carrier gas input 220 with valves V3, V8, V11B, V12A, V13, V16B and V17A permitting flow. The carrier gas backflushes precolumn 140 and injection port 190 through precolumn backflush vent 250. The carrier gas also vents analytical column 154 through detector 270 and then through detector vent 260, and analytical column 155 through analytical column vent 280, and analytical column 156 through analytical column vent 290. Then switching valves are switched to STATE 2 to inject the sample loop 210 contents onto precolumn 140 and to allow quickly-eluting sample components to enter analytical column 154, then switching valves are switched back to STATE 1 to backflush the precolumn 140 to precolumn backflush vent 250 while the sample components of interest traverse analytical column 154 and flow through detector 270.

Utilizing the switching valve positions corresponding to STATE 5, STATE 3, and STATE 5 in succession for analysis, the sample components which elute from precolumn 140 are further separated in analytical column 155 before detection. Utilizing the switching valve positions corresponding to STATE 6, STATE 4, and STATE 6 in succession for analysis, the sample components which elute from precolumn 140 are further separated on high retention analytical column 156 before detection.

A typical syringe injection analysis is performed by selecting the switching valve positions represented by STATE 7 and introducing a sample with a syringe through syringe injection port 190. Syringe injection port 190 communicates with switching valve assembly 110. The analysis proceeds with the switching valve positions represented by STATE 1 once the sample components of interest have eluted from precolumn 140 to analytical column 154. Additional separation of sample components can be achieved by switching precolumn 140 to feed analytical column 155 before the syringe injection is performed. Even more separation may be achieved by having precolumn 140 feed analytical column 156. These switching valve positions are not shown explicitly in Table 1.

An analysis to measure the total of all detectable components in the sample without any separation is performed by bypassing precolumn 140, and selecting the valve positions represented by STATE 8 and then the valve positions represented by STATE 1. It is also possible to switch portions of precolumn 140 effluent onto different analytical columns 150, and to switch analytical columns 150 to feed detector 270, at different times during the analysis to detect the desired components. This allows analysis of sample components having a wide range of retention times from the same sample.

In all analyses, the amount of sample which elutes from precolumn 140 into a selected one of analytical columns 154, 155, or 156 can be adjusted by varying the length of time during which precolumn 140 feeds selected one of analytical columns 154, 155, or 156. Valve timing in one embodiment is controlled by a computer external to analytical engine 100, such as for example, an MC 68332 microcontroller.

For sample loop 210 (see also FIG. 3) injection analyses, the amount of sample injected from sample loop 210 onto precolumn 140 can be adjusted. Adjustment of the sample amount injected can be accomplished, for example, by filling sample loop 210 by selecting the switching valve positions represented by STATE 1, selecting the switching valve positions represented by STATE 2 for a duration insufficient to allow the entire sample loop 210 to be flushed onto precolumn 140, and then selecting the switching valve positions represented by STATE 7 for the remaining duration desired for elution of the components of interest from precolumn 140.

In accordance with this invention, one embodiment uses nitrogen as a carrier gas with a flow rate of about 3 mL/minute through selected one of analytical columns 150 towards detector 270, about 3 mL/minute of maintenance flow through analytical columns 150 not selected, and about 3 mL/minute of flow for precolumn backflush. The external sample pump is typically activated for 10 to 20 seconds for each analysis, and the sample flow rate through the sample loop is about 100 mL/minute to 150 mL/minute for this interval. Hence, typical flow rates are sufficiently low not to have an appreciable effect on the thermal properties of analytical engine 100.

Figure 3:
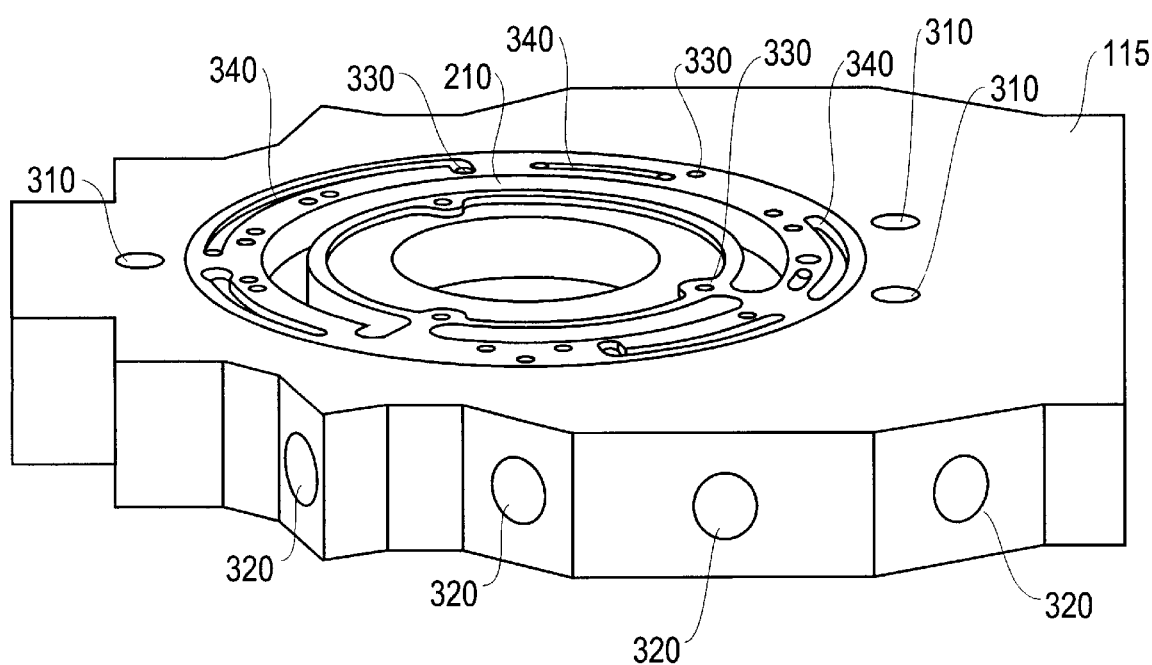
FIG. 3 shows the sample loop in the valve block of the switching valve assembly of the analytical engine in accordance with one embodiment of this invention.

FIG. 3 represents one embodiment of block 115 in accordance with this invention. FIG. 3 shows sample loop 210 which is a calibrated chamber inside block 115, alignment pin holes 310, ports 320, holes 330, and channels 340 on the top face of block 115. Ports 320, holes 330, and channels 340 provide for fluid flow (as described in the co-pending application Ser. No. 08/709,855 of Wylie and Raubvogel entitled "IMPROVED FLUID CONTROL VALVE ARRANGEMENT" referenced above) while sample loop 210 serves to store the sample prior to analysis.

In one embodiment, precolumn 140 and analytical columns 150 are coiled so that the coil diameter is between 3.0 inches and 3.25 inches, and the ends of each column are connected to the corresponding ports of valve block 115 with compression fittings having ferrules made of polyimide. Coiling fused silica columns having an inner diameter of 0.32 mm to a coil diameter smaller than 3.0 inches substantially increases the probability of fracture. Gas chromatograph detector block 175 is mounted on valve block 115 and detector block 175 communicates with a gallery (not shown) connected to valve V10 and valve V15 of FIG. 2. Galleries are connecting chambers in valve block 115. In one embodiment, detector 270 is an ultraviolet photoionization detector which is suited for detecting a wide range of gases and vapors at low concentrations. Detector 270 is vented through detector vent 260. The detector cell is formed in gas chromatograph detector block 175 with the ultraviolet lamp mounted in lamp holder 170. Gas chromatograph detector block 175 is formed of a material having high thermal diffusivity such as aluminum in one embodiment. The detector cell within detector block 175 is formed of an electrically insulating material such as, for example, tetra-fluoro-ethylene (TFE) or polyether-ether-ketone (PEEK).

Detector thermal link 180 conducts heat from the upper face of switching valve assembly 110 to detector block 175 and is formed of a material having a high thermal conductivity such as copper, in one embodiment.

In one embodiment, syringe injection port 190 fastens to a threaded hole in the upper face of switching valve assembly 110. The carrier gas in switching valve assembly 110 is routed to flow beneath a replaceable septum held in syringe injection port 190 before the carrier gas enters precolumn 140.

In accordance with this invention, temperature control for analytical engine 100 is supplied by heating element 120 mounted axially in switching valve assembly 110. Switching valve assembly 110 in one embodiment is substantially cylindrical in shape with heating element mounted at the central axis of switching valve assembly 110. Switching valve assembly 110 has a central core and upper bolt plate 118 and lower bolt plate 119 made of thermally-conductive material. In one embodiment, the central core is a hollow alloy steel bolt (not shown) and upper bolt plate 118 and lower bolt plate 119 are formed of aluminum. Heating element 120 is thereby thermally linked to the outer surfaces which include the perimeters and the upper and lower faces of upper and lower bolt plates 118 and 119, respectively, of switching valve assembly 110. In one embodiment, element 120 is a 4-ohm resistance heater with ceramic insulation in a stainless steel case having a thickness of 0.010 inch and a length of 1.5 inches with a 0.188 inch diameter. Heat is conducted radially from heating element 120 to elevate the temperature of switching valve assembly 110. Heat is also conducted radially along column plate 160, which in one embodiment is thermally linked to the lower face of switching valve assembly 110. Precolumn 140 and analytical columns 150 are positioned upon column plate 160. Because heating element 120, switching valve assembly 110, column plate 160, precolumn 140 and analytical columns 150 are substantially axisymmetric, the temperature of these elements is substantially uniform for a given radius.

Thermal cover 185 is conductively linked to the perimeter of upper bolt plate 118 of switching valve assembly 110, thereby thermally linking thermal cover 185 and upper bolt plate 118 of switching valve assembly 110. Thermal cover 185 is open at the top and extends outwards to closely enclose the upper face and the outer diameter of precolumn 140 and analytical columns 150. Thermal cover 185 is also substantially axisymmetric with switching valve assembly 110, precolumn 140, and analytical columns 150. Heat is conducted in one embodiment from upper bolt plate 118 of switching valve assembly 110, along thermal cover 185 and from the lower face of switching valve assembly 110 to column plate 160 to convectively heat precolumn 140 and analytical columns 150, thereby thermally linking the gas chromatograph columns to switching valve assembly 110. The circular symmetry of analytical engine 100 provides for uniformity of the predominantly convective heating of precolumn 140 and analytical columns 150. Thermal cover 185 and column plate 160 are beneficially formed from a metal with a high thermal conductivity such as copper, for example, in one embodiment.

Figure 1B:
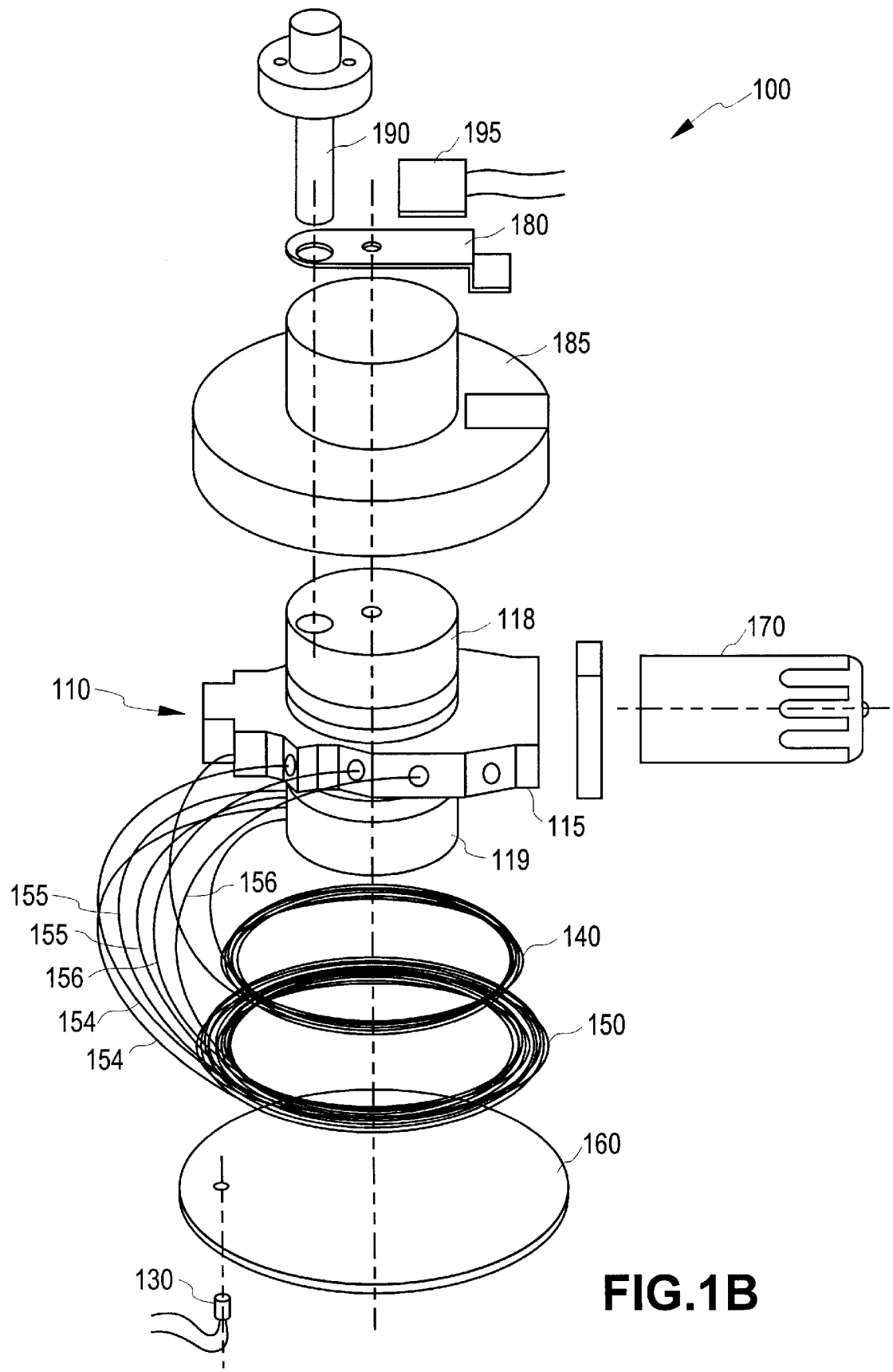
FIG. 1b shows an exploded view of analytical engine for gas chromatography having a Peltier cooler in accordance with an embodiment of this invention.
Figure 1C:
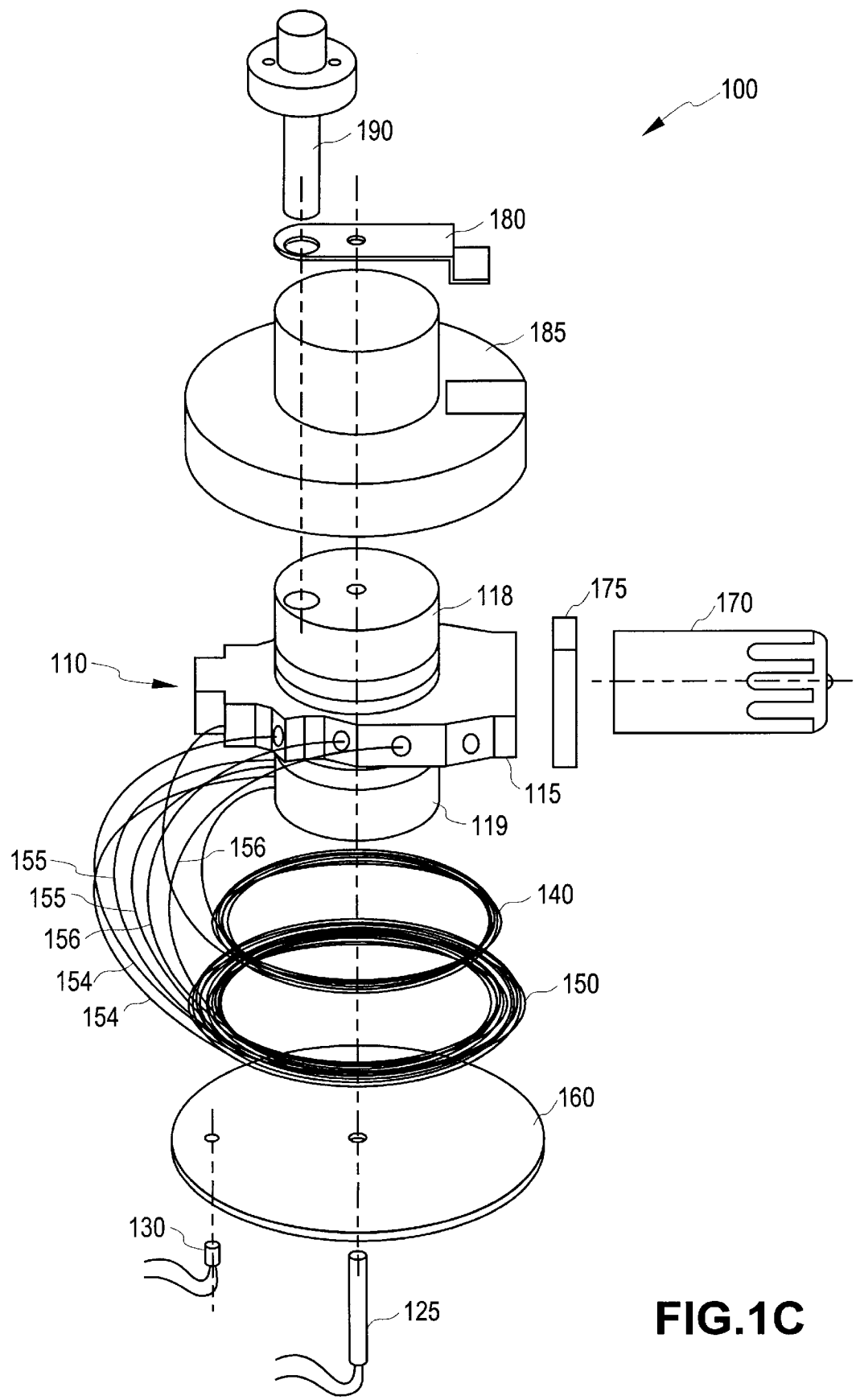
FIG. 1c shows an exploded view of an analytical engine for gas chromatography having a heat pipe in accordance with an embodiment of this invention.

If a cooler such as a Peltier cooler (see FIG. 1*b*) or a heat pipe (see FIG. 1*c*) is used for cooling in an embodiment, the heat flows will be the reverse of the heat flow in the heater configuration. Peltier cooler 195 (FIG. 1*b*) is thermally linked with and positioned on detector thermal link 180. Heat pipe 125 (FIG. 1*c*) extends through analytical engine 100 and connects at both ends to a means for circulating either a cold or a hot fluid through analytical engine 100. Very light gases can be analyzed by using a cooler rather than a heater mounted in analytical engine 100, so that a sub-ambient temperature can be maintained. The temperature of analytical engine 100 may be raised in a controlled manner during analysis so that sample components with a wider range of retention times may be analyzed in the same analysis.

Temperature sensor 130 is positioned in one embodiment on the underside of column plate 160 beneath precolumn coil 140 and analytical column coils 150 to regulate the temperature of analytical engine 100 at the columns and provide a high degree of repeatability of retention times. In one embodiment, temperature sensor 130 is a platinum resistance device. Temperature control is typically managed by an external computer and an electric power supply. In accordance with this invention, one embodiment of analytical engine 100 requires a power level of 15.2 watts for 20 minutes to bring analytical engine 100 from an ambient temperature of 20° C. to an operating temperature of 60° C. Once analytical engine 100 has achieved an operating temperature of 60° C., 3.2 watts are consumed to maintain a 60° C. operating temperature in a 20° C. ambient environment.

Analytical engine 100 is housed in an enclosure (not shown) of thermally insulating material. In one embodiment, column plate 160 sits on a 0.375 inch thick sheet of polyimide fiberboard and a 0.5 inch thick sheet of open cell melamine (not shown) and thermal cover 185 and detector thermal link 180 are covered with a bonnet (not shown) of open-cell melamine. Lamp holder 170 is also insulated with open-cell melamine. Circular holes of minimum diameter are provided in the enclosure (not shown) for access to injection port 190 and to detector lamp holder 170.

The various embodiments of the structure of this invention that are described above are illustrative only of the principles of this invention and are not intended to limit the scope of the invention to the particular embodiments described. In view of this disclosure, those skilled-in-the-art can define many other configurations of switching valves, chromatographic columns, and detectors according to the principles of this invention. For example, multiple columns and detectors can be used in parallel to permit multiple analyses to occur concurrently. Also two detectors of different types such as a photoionization detector and an electron-capture detector may be used in series or parallel to allow the relative response of the sample component on each detector to be used to identify the component and thereby increase the confidence in the sample component identification. Analysis time may be reduced by injecting portions of the same sample from a sample loop onto two different precolumn and analytical column pairs so that little-retained and much-retained sample components can be analyzed concurrently. Those skilled-in-the-art will also see application of the analytical engine to other types of chromatographic instruments where temperature uniformity is important, such as liquid chromatographs and supercritical fluid chromatographs.

We claim:

1. An analytical engine for analyzing gas and/or vapor composition and/or concentration, comprising:

a switching valve assembly;

a column plate in close proximity to said switching valve assembly, said column plate being thermally linked to said switching valve assembly;

a thermal cover in close proximity to said switching valve assembly, said thermal cover being thermally linked to said switching valve assembly and substantially coaxial with said switching valve assembly; and an analytical column positioned in close proximity to said switching valve assembly and said column plate, said analytical column being thermally linked to each of said switching valve assembly, said thermal cover, and said column plate, and said analytical column being within an enclosure that includes said thermal cover and said column plate.

2. The analytical engine of claim 1 wherein said analytical column is positioned substantially circumferentially and axisymmetric to said switching valve assembly.

3. The analytical engine of claim 1 wherein said switching valve assembly further comprises a valve block, said valve block being coupled to a detector block, with said detector block being thermally linked to said switching valve assembly by a detector thermal link.

4. The analytical engine of claim 3 wherein said valve block comprises at least one membrane valve.

5. The analytical engine of claim 1 wherein a syringe injection port is proximate to said switching valve assembly.

6. The analytical engine of claim 1 wherein said thermal cover and said column plate are each formed of a material having high thermal conductivity.

7. The analytical engine of claim 6 wherein said material having high thermal conductivity is copper.

8. The analytical engine of claim 1 further comprising an electric heater.

9. The analytical engine of claim 8 wherein said electrical heater is mounted in and axially aligned with said switching valve assembly.

10. The analytical engine of claim 9 wherein said electrical heater consumes less than 8 watts of power to maintain the analytical engine at operating temperature in a 20° C. ambient environment.

11. An analytical engine for analyzing gas and/or vapor composition and/or concentration, comprising:
   a switching valve assembly comprising:
      a first face that defines and covers a geometric interior;
      a second face that defines and covers the geometric interior;
      a perimeter that defines and covers the geometric interior; and
      a valve block;
   a column plate in close proximity to said first face, said column plate thermally linked to said first face;
   a thermal cover in close proximity to said perimeter, said thermal cover being thermally linked to said perimeter and substantially coaxial with said switching valve assembly;
   a plurality of gas chromatograph columns positioned substantially coaxial to said switching valve assembly and in close proximity to said column plate, said plurality of gas chromatograph columns being thermally linked to each of said switching valve assembly, said thermal cover and said column plate; and
   a detector block coupled to said valve block, said detector block being thermally linked to said second face by a detector thermal link.

12. The analytical engine of claim 11 further comprising a means for controlling temperature.

13. The analytical engine of claim 12 wherein said means for controlling temperature is a Peltier cooler.

14. The analytical engine of claim 12 wherein said means for controlling temperature is an axial heat pipe.

15. The analytical engine of claim 12 wherein said means for controlling temperature is an axially aligned and axially mounted electric heating element.

16. The analytical engine of claim 11 wherein selected ones of said plurality of gas chromatograph columns may be selectively in communication with said detector block.

17. The analytical engine of claim 11 wherein said detector block is made of aluminum.

18. The analytical engine of claim 11 wherein one of said plurality of gas chromatograph columns is a precolumn which can be backflushed for cleaning.

19. The analytical engine of claim 11 wherein a maintenance flow can be provided through unselected ones of said plurality of gas chromatograph columns.

20. The analytical engine of claim 11 wherein a temperature sensor is mounted proximate to said column plate.

21. The analytical engine of claim 20 wherein said temperature sensor is a platinum resistance device.

22. The analytical engine of claim 11 wherein a detector is mounted in said detector block.

23. The analytical engine of claim 22 wherein said detector is an ultraviolet photoionization detector.

24. The analytical engine of claim 22 wherein said detector is an electron-capture detector.

25. An analytical engine for analyzing gas/or vapor composition and/or concentration comprising the following components in an integral assembly: a switching valve assembly, a gas chromatograph column coupled to said switching valve assembly, and a temperature control element that passes through an interior of and is axially aligned with said switching valve assembly and provides heating or cooling.

26. An analytical engine for analyzing gas and/or vapor composition and/or concentration, comprising:
   a switching valve assembly;
   a gas chromatograph column mechanically coupled to said switching valve assembly; and
   a substantially cylindrical temperature control element axially aligned with at least one of said switching valve assembly and said gas chromatograph column, wherein said temperature control element extends into a geometric region surrounded by at least one of said switching valve assembly and said gas chromatograph column, and said temperature control element heats or cools said gas chromatograph column.

27. The analytical engine of claim 26 wherein said temperature control element is axially aligned with said switching valve assembly.

28. The analytical engine of claim 27 wherein said temperature control element passes through an interior of said switching valve assembly.

29. The analytical engine of claim 26 wherein said temperature control element is axially aligned with said gas chromatograph column.

30. The analytical engine of claim 29 wherein said temperature control element passes through a circumferential region surrounded by said gas chromatograph column.

31. The analytical engine of claim 26 further including an enclosure that surrounds said switching valve assembly and said gas chromatograph column and is axially aligned with said temperature control element.

32. The analytical engine of claim 26 wherein said temperature control element heats said gas chromatograph column.

33. The analytical engine of claim 26 wherein said temperature control element cools said gas chromatograph column.

34. An analytical engine for analyzing composition and/or concentration of a gas and/or vapor injected into a switching valve assembly, comprising:
   a switching valve assembly;
   a gas chromatograph column mechanically coupled to said switching valve assembly; and
   an electronic temperature control element axially aligned with at least one of said switching valve assembly and said gas chromatograph column, wherein said temperature control element extends into a geometric region surrounded by at least one of said switching valve assembly and said gas chromatograph column, and said temperature control element heats or cools said gas chromatograph column.

35. An analytical engine for analyzing gas and/or vapor composition and/or concentration comprising:
   a switching valve assembly;
   a gas chromatograph column mechanically coupled to said switching valve assembly;
   an enclosure that surrounds and is adjacent to and is thermally linked to said gas chromatograph column; and a Peltier cooler outside said enclosure and thermally linked to said switching valve assembly and said gas chromatograph column.

36. An analytical engine for analyzing gas and/or vapor composition and/or concentration comprising the following components in an integral assembly:
   a switching valve assembly; and
   a plurality of gas chromatograph columns, wherein each of said gas chromatograph columns is mechanically coupled to said switching valve assembly, and said switching valve assembly can provide an analytical flow through a selected one of said gas chromatograph columns and a maintenance flow through unselected ones of said gas chromatograph columns.

37. An analytical engine for analyzing gas and/or vapor composition and/or concentration comprising the following components in an integral assembly:
   a switching valve assembly; and
   a gas chromatograph column mechanically coupled to said switching valve assembly; and
   a detector mounted in a detector block in close proximity to and mechanically coupled to said switching valve assembly.

38. The analytical engine of claim 37 wherein said detector block is coupled to a valve block in said switching valve assembly.

39. The analytical engine of claim 37 wherein said detector block is thermally linked to said switching valve assembly by a detector thermal link.

40. The analytical engine of claim 37 wherein said detector block is coupled to a valve block in said switching valve assembly, and a detector thermal link is coupled to said detector block and said switching valve assembly.

41. The analytical engine of claim 37 wherein said detector is a ultraviolet photoionization detector.

42. The analytical engine of claim 37 wherein said detector is an electron-capture detector.

43. An analytical engine for analyzing gas and/or vapor composition and/or concentration, comprising:
   a thermaly conductive housing;
   a switching valve assembly within said housing; and
   a gas chromatograph column mechanically coupled to said switching valve assembly and within and in thermal and mechanical contact with said housing.

44. An analytical engine for analyzing gas and/or vapor composition and/or concentration, comprising the following components, fitted together, to form an integral assembly:
   a thermally conductive housing;
   a switching valve assembly within and in thermal and mechanical contact with said housing; and
   a gas chromatograph column mechanically coupled to said switching valve assembly and within and thermally linked to said housing.

45. An analytical engine for analyzing gas and/or vapor composition and/or concentration, comprising the following components, fitted together, to form an integral assembly:
   a thermally conductive housing;
   a substantially cylindrical switching valve assembly within and in thermal and mechanical contact with said housing; and
   a gas chromatograph column mechanically coupled to said switching valve assembly and within and in thermal contact with said housing.

46. The analytical engine of claim 45 wherein said gas chromatograph column is in thermal and mechanical contact with a column plate of said housing.

47. The analytical engine of claim 45 wherein said gas chromatograph column is substantially coaxial with said switching valve assembly.

48. An analytical engine for analyzing gas and/or vapor composition and/or concentration, comprising:
   an enclosure that includes a thermal cover as an upper portion and a column plate as a lower portion;
   a switching valve assembly within said enclosure, wherein said switching valve assembly includes a perimeter adjacent to and thermally linked to said thermal cover, and said switching valve assembly includes a lower face adjacent to and thermally linked to said column plate; and
   a gas chromatograph column substantially coaxial with said switching valve assembly, within said enclosure, and adjacent to and thermally linked to said column plate.

49. An analytical engine for analyzing gas and/or vapor composition and/or concentration, comprising:
   a switching valve assembly;
   a column plate adjacent to and thermally linked to said switching valve assembly;
   a thermal cover adjacent to and thermally linked to and substantially coaxial with said switching valve assembly; and
   an analytical column substantially coaxial with said switching valve assembly, adjacent to said column plate, thermally linked to each of said switching valve assembly, said thermal cover, and said column plate, and within an enclosure that includes said thermal cover as an upper portion and said column plate as a lower portion.

50. An analytical engine for analyzing gas and/or vapor composition and/or concentration comprising:
   a switching valve assembly comprising:
      a first face that defines and covers a geometric interior;
      a second face that defines and covers the geometric interior;
      a perimeter that defines and covers the geometric interior; and
      a valve block;
   a column plate adjacent to and thermaly linked to said first face;
   a thermal cover adjacent to and thermally linked to said perimeter and substantially coaxial with said switching valve assembly;
   a plurality of gas chromatograph columns positioned substantially coaxial to said switching valve assembly, adjacent to said column plate, and thermally linked to each of said switching valve assembly, said thermal cover and said column plate; and
   a detector block coupled to said valve block and thermally linked to said second face by a detector thermal link.

51. An analytical engine for analyzing gas and/or vapor composition and/or concentration comprising the following components in an integral assembly:
   an external housing that includes a thermally conductive enclosure;
   a switching valve assembly within said enclosure;
   a temperature control element within said enclosure; and
   a gas chromatograph column mechanically coupled to said switching valve assembly and within and in thermal contact with said enclosure, wherein a temperature of said enclosure, said switching valve assembly and said gas chromatograph column is substantially uniform for a given radius from a center of said enclosure.

52. The analytical engine of claim 51 wherein said temperature of said enclosure, said switching valve assembly, said gas chromatograph column and said temperature control element is substantially uniform for said given radius.

53. The analytical engine of claim 52 wherein said enclosure, said switching valve assembly, said gas chromatograph column and said heating element are substantially axisymmetric.

54. The analytical engine of claim 51 wherein said housing includes a thermally insulative material that surrounds said enclosure and is exposed to the ambient.

55. The analytical engine of claim 54 wherein said enclosure includes a thermal cover and a column plate.

56. The analytical engine of claim 54 wherein said thermally insulative material is open-cell melamine and said enclosure is a high thermal conductivity metal.

57. An analytical engine for analyzing gas and/or vapor composition and/or concentration comprising the following components in an integral assembly:
an external housing that includes a thermally conductive enclosure;
a switching valve assembly within said housing;
a temperature control element within said housing; and
a gas chromatograph column mechanically coupled to said switching valve assembly and within and in thermal contact with said enclosure, wherein said enclosure transfers heat between said temperature control element and said gas chromatograph column.

58. The analytical engine of claim 57 wherein said housing includes a thermally insulative material that surrounds said enclosure and is exposed to the ambient.

59. The analytical engine of claim 58 wherein said enclosure includes a thermal cover and a column plate.

60. The analytical engine of claim 58 wherein said thermally insulative material is open-cell melamine and said enclosure is a high thermal conductivity metal.

61. An analytical engine for analyzing gas and/or vapor composition and/or concentration comprising the following components in an integral assembly:
an external housing that includes a thermally conductive enclosure;
a switching valve assembly within said enclosure;
a temperature control element outside said enclosure; and
a gas chromatograph column mechanically coupled to said switching valve assembly and within and in thermal contact with said enclosure, wherein a temperature of said enclosure, said switching valve assembly and said gas chromatograph column is substantially uniform for a given radius from a center of said enclosure.

62. The analytical engine of claim 61 wherein said temperature control element is a Peltier cooler.

63. The analytical engine of claim 61 wherein said enclosure, said switching valve assembly and said gas chromatograph column are substantially axisymmetric.

64. The analytical engine of claim 61 wherein said housing includes a thermally insulative material that surrounds said enclosure and is exposed to the ambient.

65. The analytical engine of claim 64 wherein said enclosure includes a thermal cover and a column plate.

66. The analytical engine of claim 64 wherein said thermally insulative material is open-cell melamine and said enclosure is a high thermal conductivity metal.

67. An analytical engine for analying gas and/or vapor composition and/or concentration, comprising:
an external housing that includes a thermally conductive enclosure;
a switching valve assembly within said housing;
a temperature control element outside said housing; and
a gas chromatograph column mechanically coupled to said switching valve assembly and within and in thermal contact with said enclosure, wherein said enclosure transfers heat between said temperature control element and said gas chromatograph column.

68. The analytical engine of claim 67 wherein said housing includes a thermally insulative material that surrounds said enclosure and is exposed to the ambient.

69. The analytical engine of claim 68 wherein said enclosure includes a thermal cover and a column plate.

70. The analytical engine of claim 68 wherein said thermally insulative material is open-cell melamine and said enclosure is a high thermal conductivity metal.

* * * * *